US00PP26212P3

(12) United States Plant Patent
Growns

(10) Patent No.: US PP26,212 P3
(45) Date of Patent: Dec. 15, 2015

(54) WAXFLOWER PLANT NAMED 'WX 56'

(50) Latin Name: ***Chamelaucium* hybrid *(Chamelaucium megalopetalum×Chamelaucium uncinatum)***
Varietal Denomination: WX 56

(71) Applicant: Western Australian Agriculture Authority, Bentley (AU)

(72) Inventor: Digby Growns, Kings Park (AU)

(73) Assignee: Western Australian Agriculture Authority, Bently (AU)

( * ) Notice: Subject to any disclaimer, the term of this patent is extended or adjusted under 35 U.S.C. 154(b) by 143 days.

(21) Appl. No.: 13/987,941

(22) Filed: Sep. 16, 2013

(65) Prior Publication Data

US 2014/0082791 P1 Mar. 20, 2014

Related U.S. Application Data

(60) Provisional application No. 61/744,180, filed on Sep. 19, 2012.

(51) Int. Cl.
*A01H 5/02* (2006.01)

(52) U.S. Cl.
USPC ..... Plt./226
CPC ..... *A01H 5/02* (2013.01)

(58) Field of Classification Search
USPC ..... Plt./226
See application file for complete search history.

(56) References Cited

PUBLICATIONS van der Ploeg, R., "Exciting developments in waxflower breeding and marketing," Sep. 2011; www.FloraCultureInternational.com—file retrieval on Mar. 28, 2015 (3 pages total).*
www.wafex.com.au/pages/about_wafex/news/2011-09; summary of "Exciting developments in waxflower breeding and marketing," Monday, Sep. 5, 2011; file retrieval on Mar. 30, 2015 (1 page total).*
"New waxflower varieties released," Australian Flower Industry; Sep. 2011; file retrieval on Mar. 30, 2015 (1 page total).*
www.wafex.com.au/pages/about_wafex/news/2011-09; summary of "New waxflower varieties released," Thursday, Sep. 1, 2011; file retrieval on Mar. 30, 2015 (1 page total).*

* cited by examiner

*Primary Examiner* — Susan McCormick Ewoldt
(74) *Attorney, Agent, or Firm* — Michelle Bos Legal LLC

(57) ABSTRACT

'WX 56' is a new and distinct waxflower plant (interspecific *Chamelaucium* hybrid) notable for its early flowering, compact growth habit, and dense terminal cover of medium size white flowers that age to pink and then purple-red.

6 Drawing Sheets

Latin name of the genus and species of the plant claimed: Interspecific *Chamelaucium* hybrid (*Chamelaucium megalopetalum×Chamelaucium uncinatum*).

Variety denomination: 'WX 56'.

BACKGROUND OF THE INVENTION

'WX 56' is a new waxflower plant that originated as a seedling produced in a sexual breeding program conducted by the breeder at Medina and South Perth, Western Australia. 'WX 56' was selected from seedlings of a controlled cross of female parent *Chamelaucium megalopetalum* 'CM 5.5' (not patented), and male parent *C. uncinatum* '827/887-8' (not patented). An embryo was excised from fruit produced in 2000 and germinated in vitro. The resulting seedling was subcultured in tissue culture four times, deflasked, hardened and planted in the field at the research station at Medina, Western Australia in May 2001. Following flowering in July 2002, the seedling was vegetatively propagated via cuttings and a second generation of cuttings taken in March 2003 at Medina, Western Australia. A subsequent generation was propagated vegetatively in 2009. Growth and flowering records of the generations were recorded from 2002 to 2005 and again in 2010. No off-types were recorded and all plants were found to be uniform and stable.

'WX 56' is distinguishable from its female parent 'CM 5.5' by a number of features, as described in Table 1 below:

TABLE 1

| Characteristic | CM 5.5 | WX 56 |
|---|---|---|
| Flower color | White/pink aging to bright red | White aging to pink and then red/purple |
| Leaf length | Short | Medium |
| Plant height | Short | Medium |

'WX 56' is distinguishable from its male parent '827/887-8' by a number of features, as described in Table 2 below:

TABLE 2

| Characteristic | CM 827/887-8 | WX 56 |
|---|---|---|
| Flower color | Pink | White aging to pink and then red/purple |
| Leaf length | Long | Medium |
| Leaf cross-section | Round | Flattened/triangular |

'WX 56' is also distinguishable from other known waxflower varieties. Comparisons of 'WX 56' to 'WX 58' (not patented) and 'Purple Gem' (not patented), the most similar varieties of common knowledge, are set forth in Tables 3 and 4 below:

TABLE 3

| Characteristic | WX 58 | WX 56 |
|---|---|---|
| Flower color 28 days after opening | Dark purple/red | Mid red/purple |
| Flower diameter | Medium-large | Medium |
| Leaf length | Small | Medium |
| Flower colour of hypanthium day 28 | Red brown | Dark green |

TABLE 4

| Characteristic | Purple Gem | WX 56 |
|---|---|---|
| Flower color | Mottled pink/white aging to purple | White aging to pink and then to red/purple |
| Flower diameter | Small-medium | Medium |
| Leaf attitude | Semi-erect | Erect |
| Leaf cross-section | Rounded | Flattened/triangular |

BRIEF DESCRIPTION OF THE PHOTOGRAPHS

The accompanying photographs show four-year-old 'WX 56' waxflower plants growing at Medina, Western Australia during August and September (early spring) 2013.

DETAILED BOTANICAL DESCRIPTION

Figure 1:
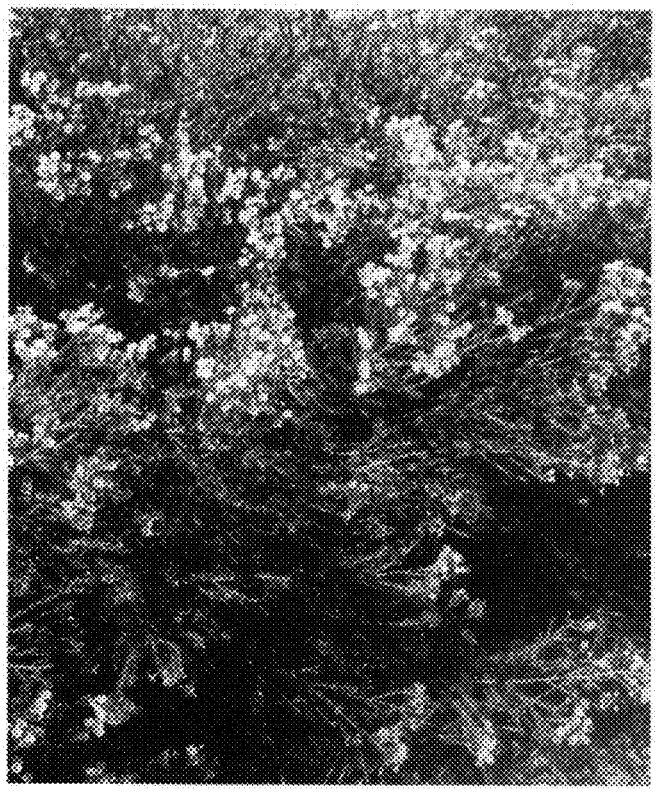
FIG. 1 is a photograph of 'WX 56' growing outdoors.
Figure 2:
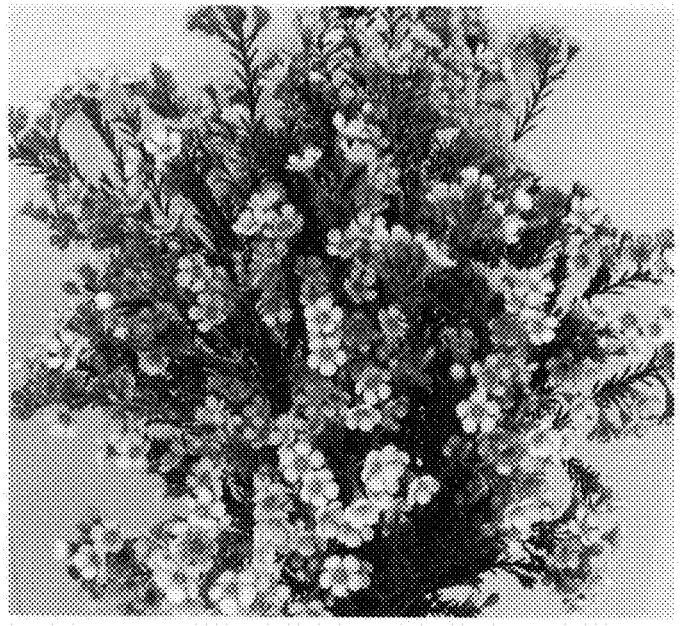
FIGS. 2, 3 and 4 are photographs of the flowers of 'WX 56'.
Figure 3:
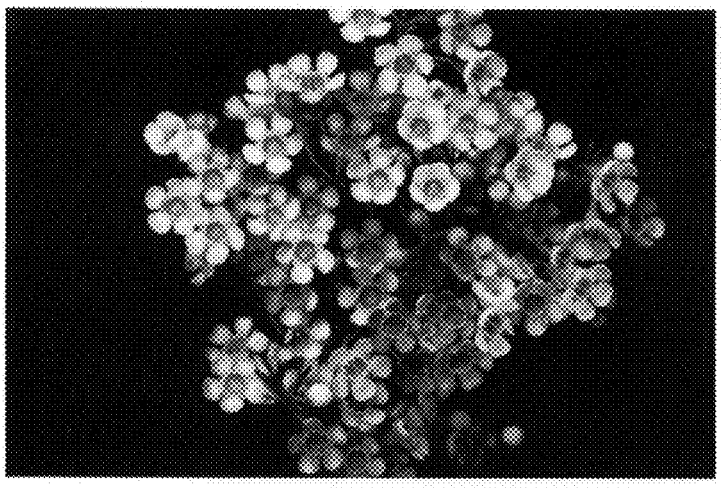
Figure 4:
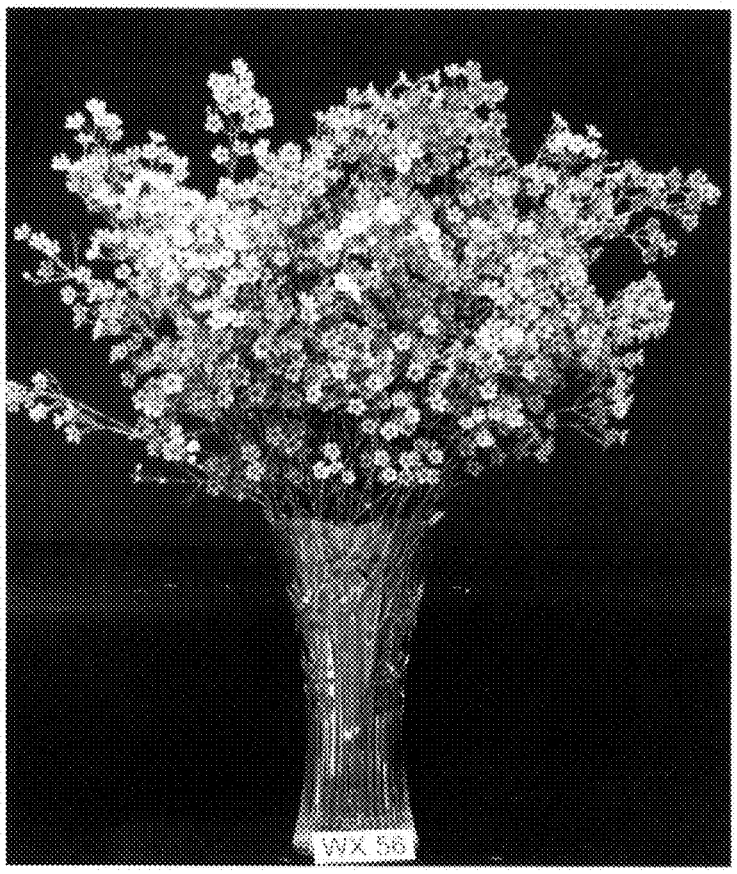
Figure 5:
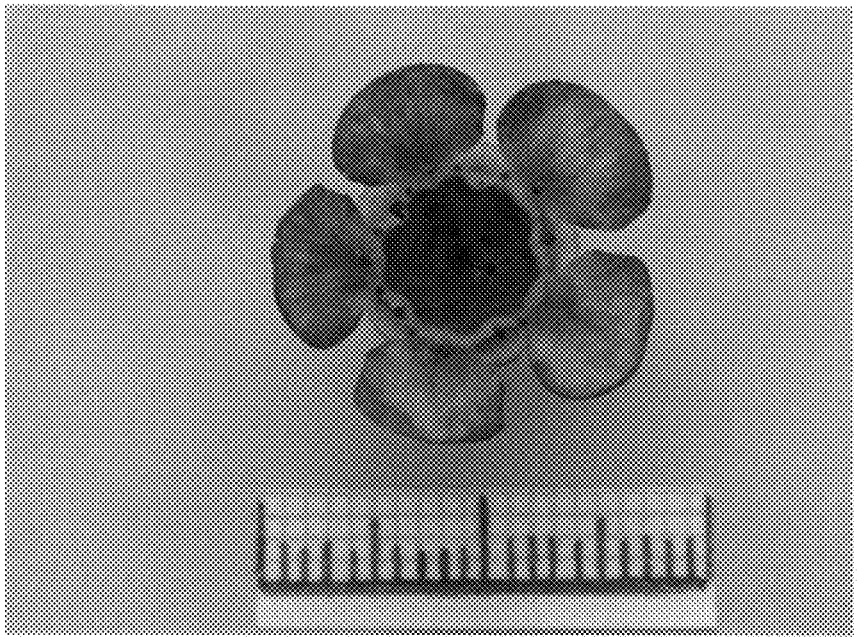
FIGS. 5 and 6 are close-up photographs of a flower of 'WX 56'.
Figure 6:
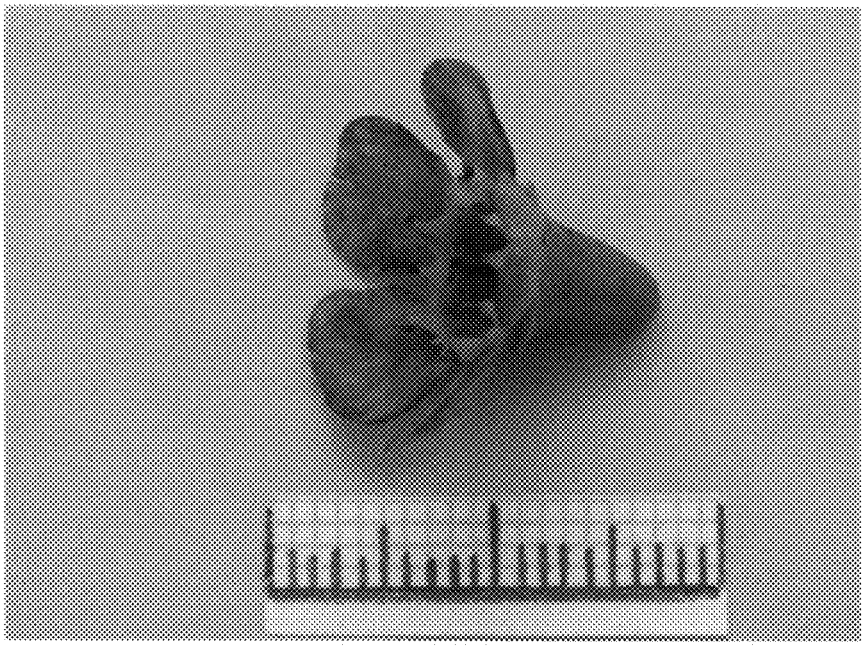
Figure 7:
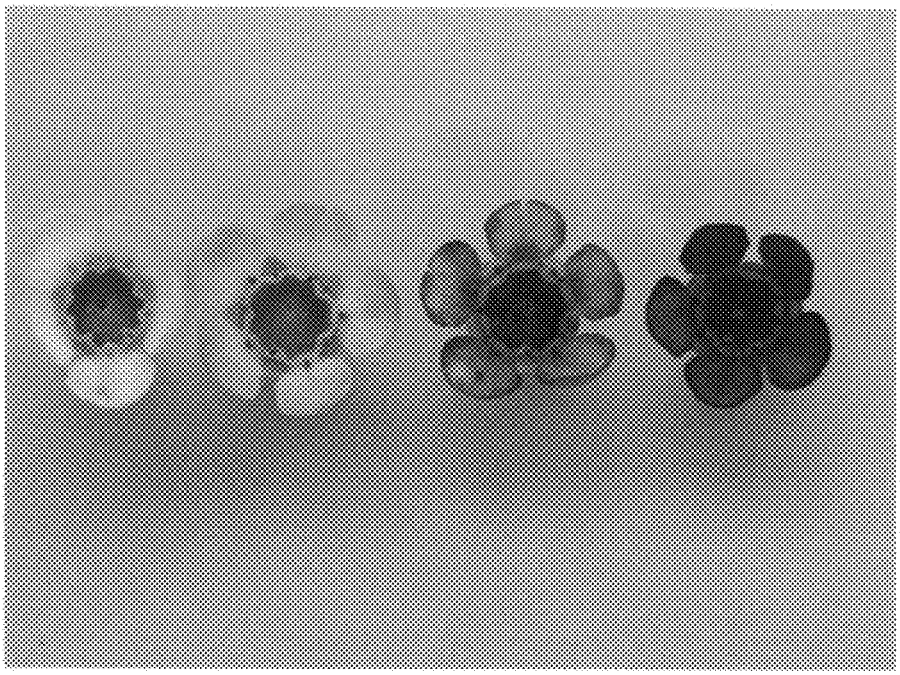
FIG. 7 is a photograph showing the typical coloration progression of flowers of 'WX 56'.
Figure 8:
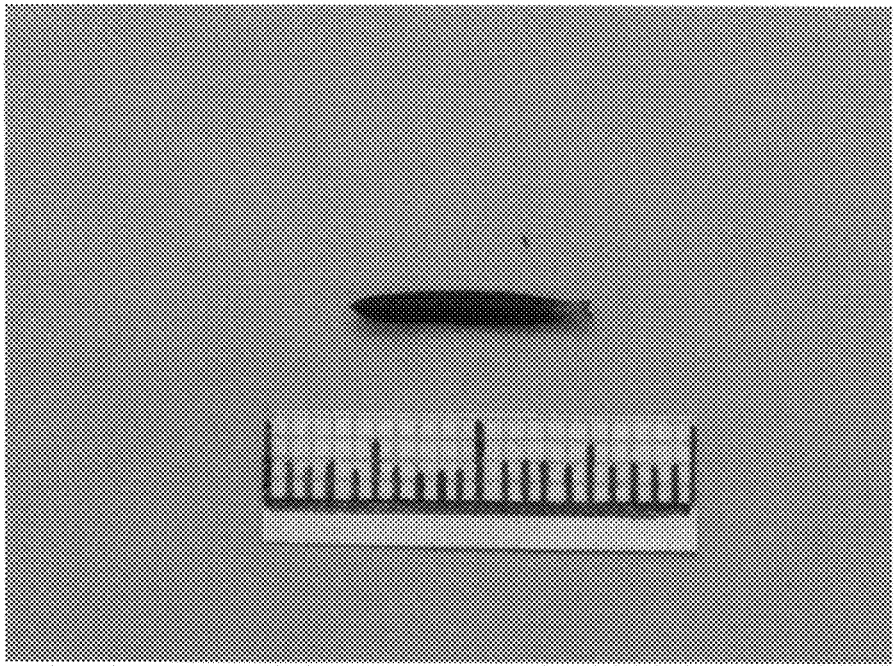
FIG. 8 is a close-up photograph of a leaf of 'WX 56'.
Figure 9:
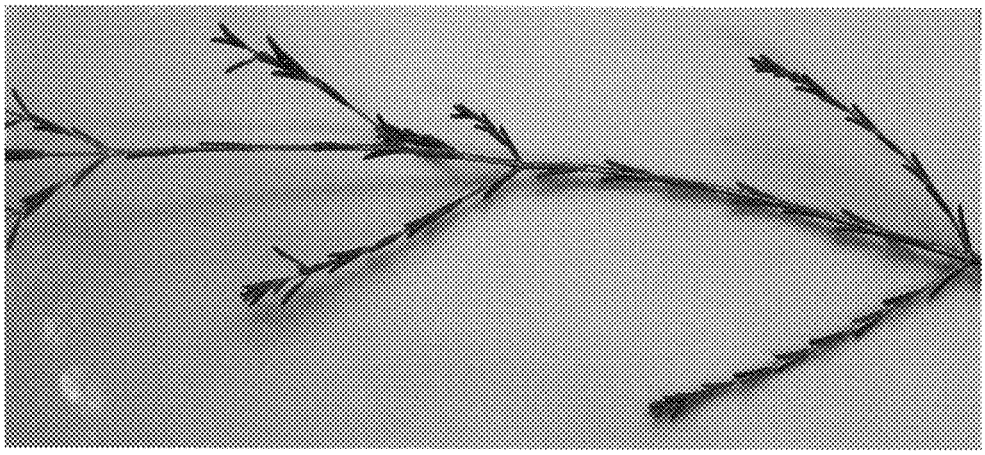
FIG. 9 is a photograph of a branch and leaves of 'WX 56'.
Figure 10:
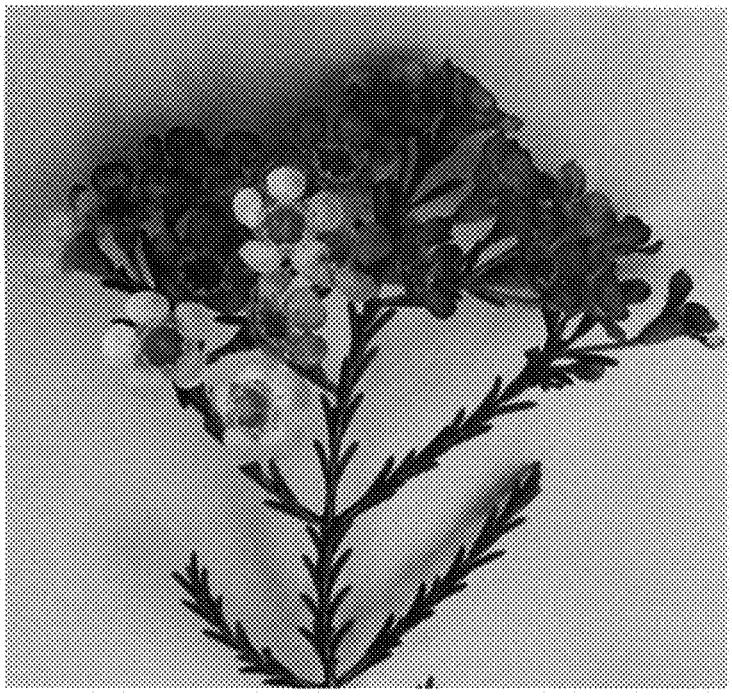
FIG. 10 is a photograph of a branch, leaves and flowers of 'WX 56'.
Figure 11:
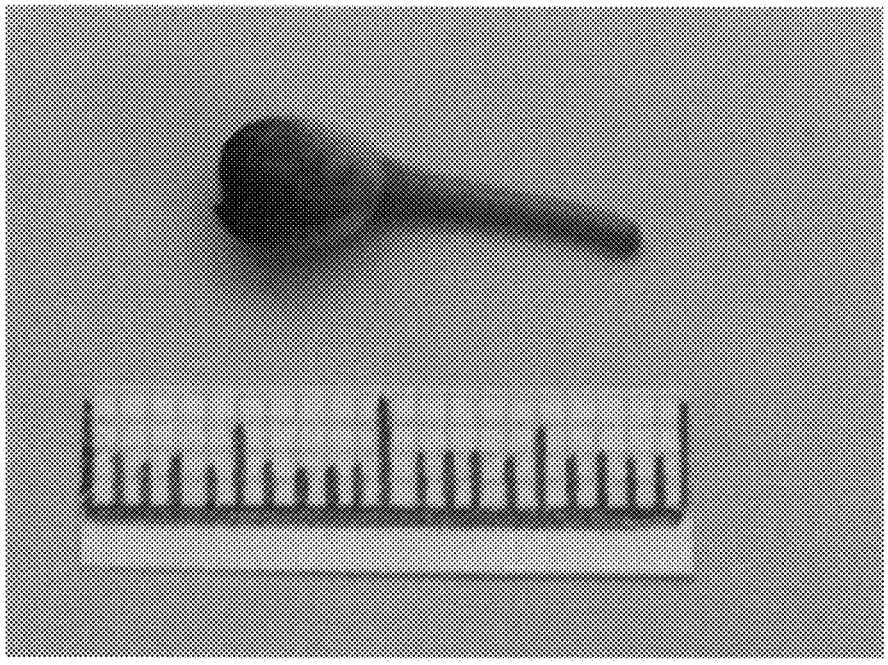
FIG. 11 is a close-up photograph of a young bud of 'WX 56'.
Figure 12:
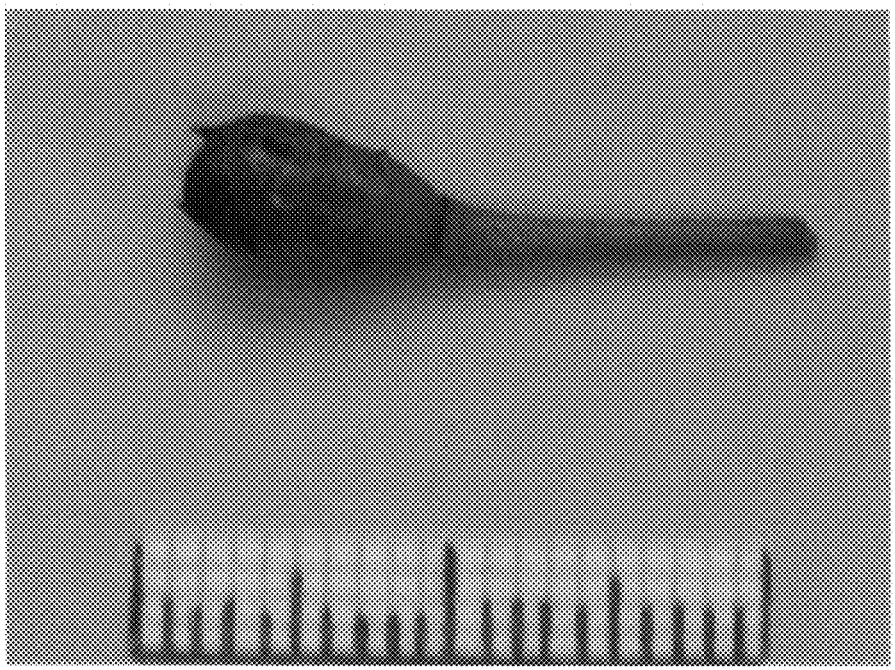
FIG. 12 is a close-up photograph of an older bud of 'WX 56'.

The following detailed botanical description is based on observations of four-year-old 'WX 56' waxflower plants growing at Medina, Western Australia during August and September (early spring) 2013, except where otherwise noted. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Plant:

*Summary*.—'WX 56' is an early flowering compact medium-height bush with dense terminal cover of medium (17 mm) white flowers that age to pink and then red/purple.

*Growth habit*.—Branching upright shrub growing to a height of 1.2 meters and bush diameter of 1.3 m.

*Flowering stem length*.—60 cm.

*Branches*.—Average of 23 main branched per plant; diameter 5.5 mm; round cross-section; smooth texture; color Grey-brown 201A and 201C. (Branch description taken from five-year-old stock plants.).

Leaves:

*Leaf arrangement*.—Opposite.

*Leaf density*.—Main branch: about 4 pairs per 6 cm branch length. Secondary branch: 8 pairs of leaves, branch 5 cm in length.

*Aroma*.—Eucalyptus or citrus aroma when leaves are crushed.

*Leaf internode length*.—Average 15.5 mm on main branch, and 11.3 mm on secondary branch.

*Leaf size*.—Length 13.5 mm, width 1.6 mm.

*Leaf shape*.—Narrowly obovate with acute apex.

*Leaf surface texture*.—Glabrous glandular, leathery, shiny.

*Leaf margin*.—Entire.

*Leaf base*.—Sessile truncate to stem.

*Leaf cross-section*.—Triangular with indented upper surface.

*Leaf color*.—New growth, upper and lower surface yellow-green 144A; mature leaves, upper and lower surface deep green 137A.

Flower:

*Flower bud*.—Fresh buds — Cone shaped with smooth shiny surface color yellow-green 145B and tip of bud color orange-red N30; diameter 4.4 mm, length 4.6 mm. Older buds — More elongated with papery operculum, coarse, surface color grey-brown N199B to N199C; diameter 4.8 mm, length 9.0 mm.

*Flowering season*.—Early July to mid August (Medina, Western Australia).

*Flower longevity*.—60 days.

*Flower quality*.—High.

*Flowering time*.—Early.

*Flower description*.—Flowers slightly cupped and petals separate when fully open, round in shape, upper and lower surface are glabrous waxy, entire margin, truncate base and fused to calyx, rounded apex. Flower color undergoes changes as it matures (lower and upper surface same coloration).

*Petal color*.—On day of opening, white 155D; 10 to 14 days after opening, red-purple 68C; Progresses to red-purple 67B; When fully developed entire petal is red-purple 64A.

*Flower arrangement*.—Corymb.

*Flower type*.—Single flower.

*Flowering habit*.—Terminal, panicle florescence.

*Flower shape*.—Cup-shaped.

*Flower diameter*.—Average 16.8 mm; depth 11.7 mm (top of stigma to bottom of ovary).

*Flowering branch angle*.—Overlapping.

*Flowering attitude of petals on day of opening*.—Semi erect.

*Flowering branch angle 2 weeks after opening*.—Semi erect.

*Flower*.—Length of sepal in relation to length of petal — Less than one-third.

*Petiole (pedicle) length*.—Long, 15 mm; aspect 12 degrees to 18 degrees.

*Hypanthium shape*.—Obconical with longitudinal furrowing on full length.

*Hypanthium diameter*.—Medium, 7.2 mm.

*Hypanthium main color at middle part*.—On day of opening of flower, yellow-green 145C; four weeks after opening of flower, yellow-green 145C red with patches of red-purple 68A to 64A.

*Nectaries*.—About 6 mm in diameter; color, see hypanthium.

*Flower petals*.—Usually 5, occasionally 6 to 7, round shape; fused sepals at base to hypanthium, with rounded outer separate lobes arranged alternately between petals; tube portion fluted; fused sepals yellow-green 145B to 146B; lobed sepals; new petals white 155D, developing an inner patch of red-purple 68A to 64A as the flower ages.

*Petal shape*.—Slightly cupped and undulation of margins weak.

*Petal texture*.—Waxy, glabrous.

*Petal dimensions*.—Slightly broader (6.9 mm) than long (6.5 mm).

*Stamen collar*.—Color at opening of flower white 155D.

*Stamen collar* 10 *to* 14 *days after opening of flower*.—Color pink 155D with red-purple 68C tinge.

*Gynoecium*.—1 pistil, stigma bearded, color yellow-green N144D with style white 155D, with patches towards tip of red-purple 63A-68C; length 6 mm.

*Androcoecium*.—About 10 fertile stamens with 10 infertile staminodes arranged alternatively on a collar adnate to junction of petals and calyx; filament length 1.3 mm, color white 155D aging to red-purple 68C with tinges of red-purple 64A; staminode length 1 mm, color white 155D aging with tinges of red-purple 64A; anthers length about 0.7 mm, color greyed-orange 166B; pollen is sterile.

Disease resistance: Moderate.

I claim:

1. A new and distinct waxflower plant substantially as shown and described herein.

* * * * *